US006711962B1

(12) United States Patent
Gerteis

(10) Patent No.: US 6,711,962 B1
(45) Date of Patent: Mar. 30, 2004

(54) METHOD AND DEVICE FOR DETERMINING THE COMPRESSION FACTOR OF POWDERS

(76) Inventor: Paul Gerteis, Hummelwaldstrasse 15, CH-8645 Jona (CH)

( * ) Notice: Subject to any disclaimer, the term of this patent is extended or adjusted under 35 U.S.C. 154(b) by 0 days.

(21) Appl. No.: 09/701,120

(22) PCT Filed: May 14, 1999

(86) PCT No.: PCT/CH99/00204

§ 371 (c)(1),
(2), (4) Date: Jan. 12, 2001

(87) PCT Pub. No.: WO99/61885

PCT Pub. Date: Dec. 2, 1999

(30) Foreign Application Priority Data

May 23, 1998 (CH) .............................................. 1125/98

(51) Int. Cl.[7] .............................................. G01N 33/00
(52) U.S. Cl. ......................................... 73/866; 73/823
(58) Field of Search .......................... 73/866, 818, 823, 73/824

(56) References Cited

U.S. PATENT DOCUMENTS 3,318,156 A * 5/1967 Dietert ......................... 73/824
3,750,467 A    8/1973 Rubio
5,140,861 A    8/1992 Gleason
5,756,907 A * 5/1998 Senda et al. .................. 73/866

FOREIGN PATENT DOCUMENTS

| EP | 0 447 156 A2 | 9/1991 |
| WO | 91 16982 A | 11/1991 |
| WO | 92 13633 A | 8/1992 |

* cited by examiner

Primary Examiner—Robert Raevis
(74) Attorney, Agent, or Firm—Michael J. Striker

(57) ABSTRACT

A method to determine the compression factor of powders for processing by roller presses with a roller diameter of 100–400 mm. A rotating press-roller (2), a matrix (4) and a piston (11) for measurement of the compression factor are used in the inventive method. The device to carry out the inventive method consists of a rotating press-roller (2) which is connected to a groove (5) in a displaceable matrix (4) and a piston (11) connected to a ruler (17) and a pointer (15) by means of a guide element (12) and a guide rod (13), whereby the depth of the groove is greater than the 20° angle tangent on the press-roller (2) when measured from the horizontal center axis.

12 Claims, 2 Drawing Sheets

METHOD AND DEVICE FOR DETERMINING THE COMPRESSION FACTOR OF POWDERS

Figure 1:
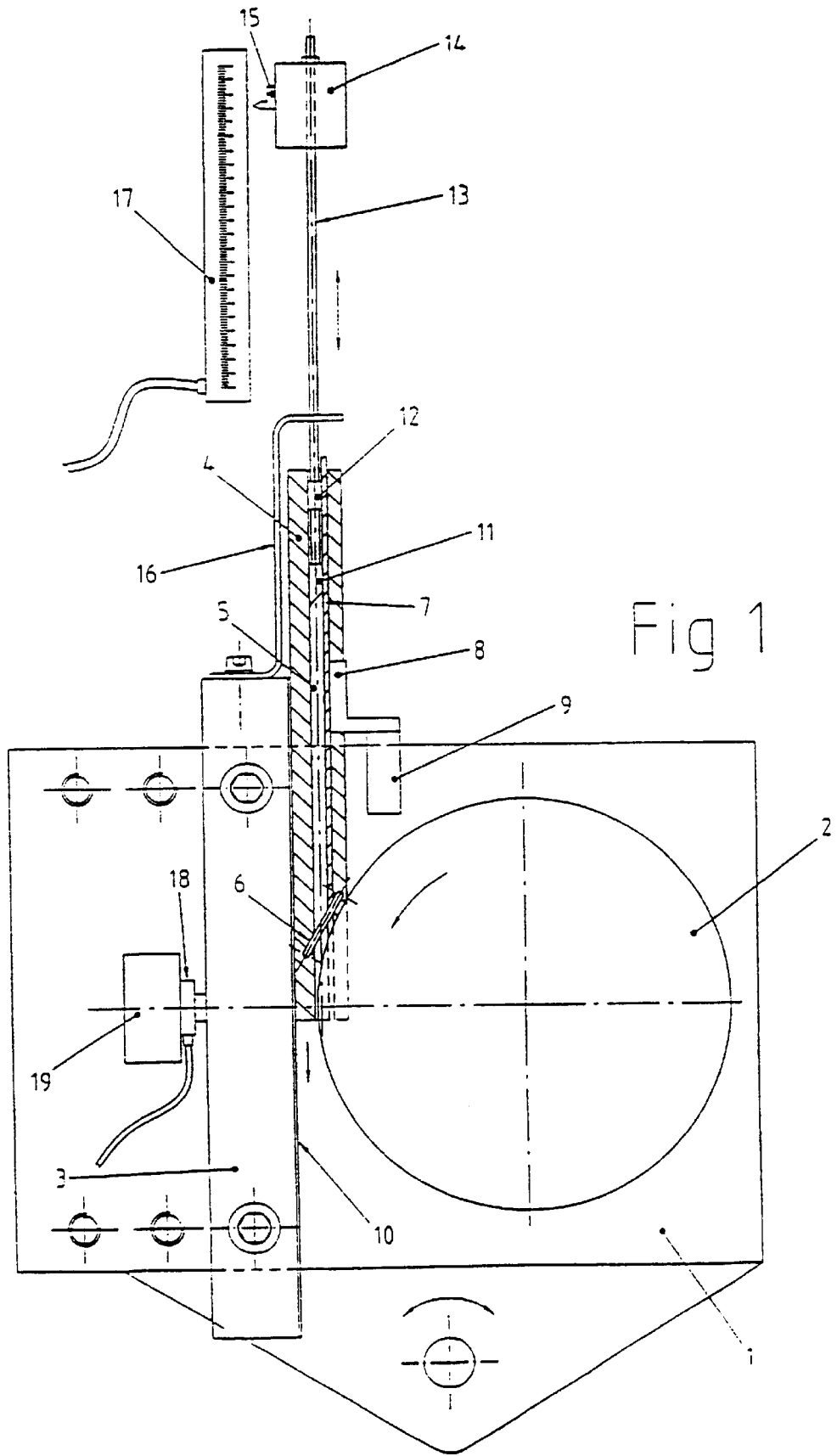

The invention relates to a method for determining the compression factor of powders for processing by means of roller presses having roller diameters of 100 to 400 mm.

Roller presses serve for pressing powders so as to form scabbed strips which are subsequently comminuted into granulate (EP-A-0 525 135). This process is referred to as the dry granulation method. The pressing of the powder takes place between 2 mutually opposed rollers, and, depending on the manufacturer, both rollers are mounted fixedly, that is to say have a fixed roller nip, or one of the two rollers is designed to be movable, is subjected to hydraulic force and has a variable roller nip.

All roller presses have at least 2 press rollers and, depending on the manufacturer, are offered with various roller dimensions. The rollers are fed with powder either by means of gravity or with the assistance of a filling worm.

The dry granulation method enjoys a special status in economic terms in the pharmaceutical industry for the production of granulate, instead of the known wet granulation method.

In the initial phase of development of a new drug, it has been necessary hitherto to dispense with development aimed at dry granulation as the most cost-effective production method, because the powder quantities required for a test are not available or are too costly. Most roller presses also lack appropriate instrumentation for obtaining useful data for the intended development.

A suitable device is known according to EP-A-0 525 135. This device delivers reproducible results even with powder quantities as low as 100 ml.

In the first development phase, only substantially smaller quantities (for example, 10 ml) are available for tests. The subsequent production method must be defined as early as at this stage.

Tablets or capsules can be produced from granulate manufactured by known methods. The most important technological properties, such as the typical entering angle and, resulting from this, the possible compression factor of the powder and also the product quantity per unit time, cannot be ascertained by tabletting.

The object of the invention is to provide a method for testing a powder for its suitability for the production of granulate by the dry granulate method with roller presses on an industrial scale.

A further object is to make available a device for carrying out the method.

The object is achieved, according to the invention, in that a rotating press roller, a die and a piston are used for measuring the compression factor.

In accordance with the present invention, a method of determining a compression factor of powders for processing by a roller presses having roller diameters of 100 to 400 mm is proposed, which comprises the steps of filling a groove of a die with powder, introducing a piston into the groove, pushing the die on a rotating press roller until it touches a roller surface, opening an end of the die located opposite to the press roller and pushing the die downward on the press roller until the powder rests on the roller surface, during a measurement exerting a force on the piston for compressing the powder, and using a position of the piston in relation to the roller for measuring a compression factor.

The advantage of the method according to the invention is that, by means of a single press roller, in combination with a die for very small powder quantities, it is possible for the first time to have predetermination for dry granulation on roller presses of all types. It makes it possible, with the least possible outlay in terms of material, to obtain the important data for a reliable prediction as regards the dry granulation method with roller presses and to keep the powder quantity required for a test as small as possible.

By the second roller being simulated, the quantity required was basically halved. Since the filling worm was dispensed with, a narrow press roller could be selected. So that the measurement can be carried out for all current roller presses of different designs, the device according to the invention has different measuring systems.

It proved particularly advantageous to compress a powder introduced in a groove in a nip predefined therein.

It is expedient to compress the powder introduced in the groove with a predefined force.

It is particularly advantageous for the groove to be formed in a displaceable die. As a result of this arrangement, a second press roller can be dispensed with.

It is expedient to move a piston provided in the groove via a guide part and a guide rod and to read off, from a rule and a pointer, a travel which represents a measured value.

The resulting press force is measured in the case of a permanently predefined roller nip.

The resulting roller nip is measured in the case of a permanently predefined press force.

In the device, the rotating press roller is assigned a groove in a displaceable die and a piston via a guide part and a guide rod, a rule and a pointer. The advantage of this is that only a single press roller is required, with the result that the device is very simple. This device is suitable for determining the compression factor of powders, irrespective of the origin of a roller press.

On roller presses, because the press rollers are arranged in pairs, the typical entering angle is active in each case on the left and on the right roller, but is required only once for assessment.

The unit of measurement for the highest press force exerted instantaneously on the powder is: kN/cm of linear roller width. This force is applied at a theoretical line transversely to the roller at the location where the two rollers are nearest. So that as little powder as possible is required, this method employs rollers with a width of 1 cm. Wider rollers may also be used for comparative measurements, such as, for example, for scale-up validation.

So that behavior can be tested in the case of different roller diameters, the abutment may be mounted in different positions, so that press roller diameters of 100 to 400 mm from the various manufacturers can be simulated.

Figure 2:
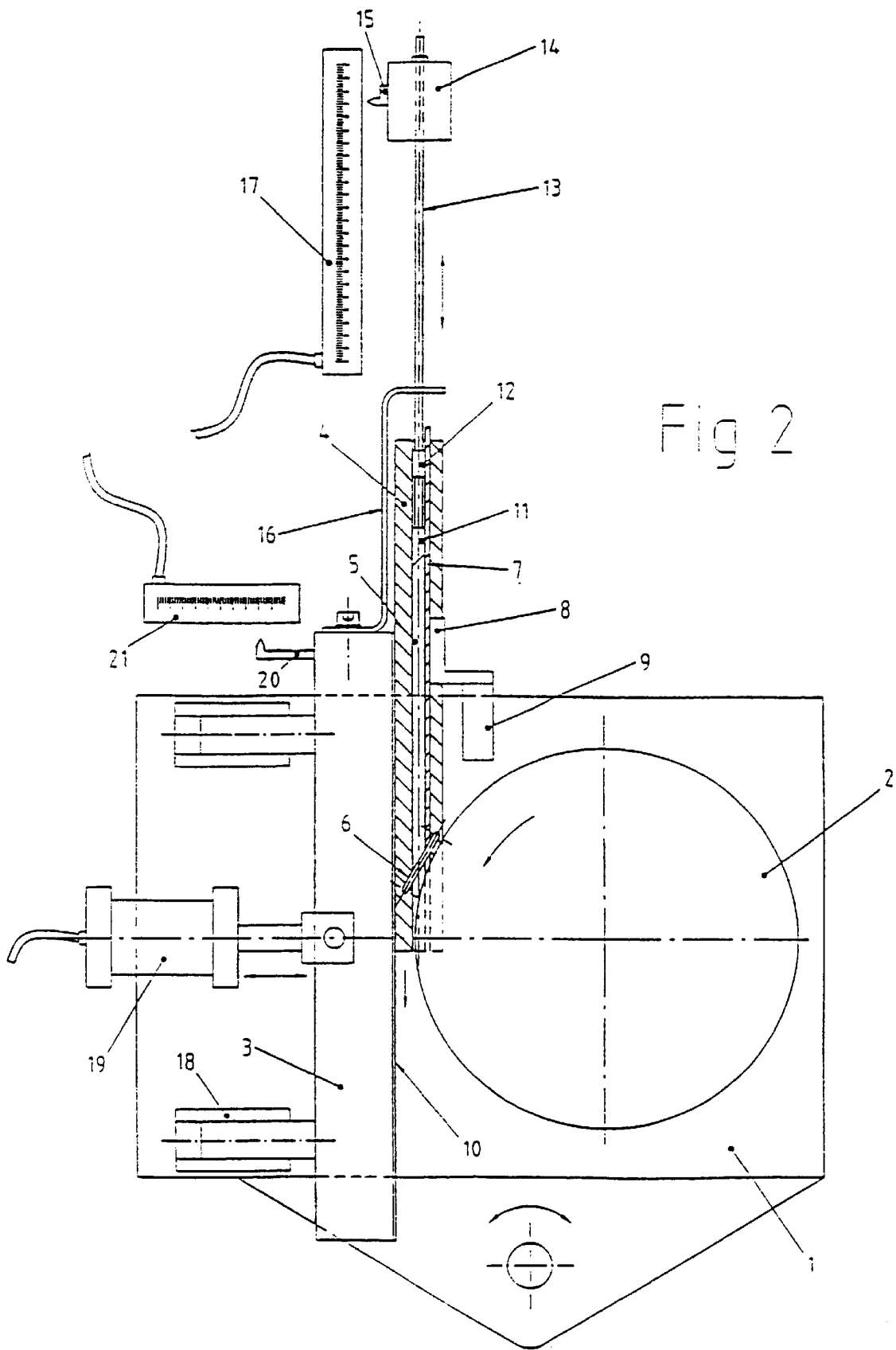

The invention will be described in more detail by means of a drawing in which:

FIG. 1 shows the device according to the invention in cross section for measurement in the case of a defined roller nip and the resulting press force FIG. 2 shows a variant of the device according to the invention for measurement in the case of a defined press force and the resulting roller nip.

In FIG. 1, a bearing block is designated by the reference symbol 1. Located in the bearing block 1 is the motor-driven drive shaft which cannot be seen and on which an exchangeable press roller 2 is mounted. An abutment 3 capable of being mounted in different positions is likewise mounted, as a stationary carrier for a sliding surface 10 of variable thickness, on the bearing block 1. A die 4 is provided with a groove 5 which is wider than the width the press roller 2. The depth of the groove 5 is greater than a 20 degree angle tangent to the press roller, as measured from the horizontal center axis. A transverse slide 6 running tangentially to the roller surface seals off the die 4 downward and prevents the powder from flowing out undesirably prior to measurement. The groove 5 is covered with a longitudinal slide 7. A stop 8 is set in its vertical position on the clamping piece 9. A piston 11 seals off the groove 5 upward. A guide part 12 prevents the piston 11 from tilting in the groove 5. A guide part 12 and a piston 11 are mounted on the guide rod 13. A tared weight 14 having a permanently installed pointer 15 is mounted at the upper end of the guide rod 13. A holder 16 stabilizes the guide rod 13 in its vertical position. A scale 17 makes it possible to read off the respective position of the piston before and after the process and to evaluate this position for the calculation. Travel measurement may also be carried out electronically or optically. A load cell 18 is mounted between the back of the abutment 3 and a retention means 19.

In FIG. 2, the method is simulated by roller presses which are provided with a permanently defined press force and a variable roller nip. In this variant of the device, the displacement of the abutment 3 relative to the press roller is additionally indicated and read off on a scale 21 via a pointer 20. Travel measurement may also be carried out electronically or optically.

In each version, the device may be arranged at an angle of between 0 and 90 degrees out of the horizontal axis, so that all customary roller types can be simulated.

2 methods are customary for the measurement.
Measuring Method 1:

Either loosely dumped powder, that is to say the basis is the dumping volume of a powder or of a powder mixture, may be tested for compacting behavior or, according to
Measuring Method 2

The die together with the loosely dumped powder or powder mixture can be precompressed on a calibrated tamping volumenometer at 1250 strokes according to an acknowledged method for determining the tamping volume.

During operation, for filling, the die 4 is laid horizontally onto a clean suitable base. The groove 5 opened upward is filled with powder.

After the powder has been introduced into the groove 5 of the die 4, the transverse slide 6 and the longitudinal slide 7 are pushed into their guides and the piston 11 is introduced. As a result of the introduction of the transverse slide 6, of the longitudinal slide 7 and of the piston 11, the powder space is closed. The die 4 is raised and pushed toward the press roller 2, until the transverse slide 6 touches the roller surface and the die comes to bear, on its rear closed side, against the abutment 3. The transverse slide 6 is then removed and the die 4 is pushed downward toward the press roller 2 until the powder comes to bear against the roller surface. The stop 8 of the longitudinal slide 7 will simultaneously come to bear on the support 9. At this moment, the position of the pointer 15 against the scale 17 is tared and the zero point is thus set.
Definition of the Measuring Operation:

If the travel covered on the circumference of the forward-rotating press roller 2 is equal to the travel of the downward-moving die 4 and of the piston 11, this means that the entire powder quantity introduced has been compressed.

Roller nip=1 mm

The formula:

$$\frac{5}{1} \cdot \frac{100}{100+0}$$

yields a compression factor=5

The entering angle can be read off from a table.

A differential value between the travel of the piston 11 and that on the circumference of the press roller 2, which is equal to the travel of the die 4 is obtained when the powder, because of its changed entering behavior, allows a lower entering angle and therefore causes a recoil value on the piston 11. This recoil value is indicated and read off on the rule 17 via the piston 11, the guide rod 13 and the pointer 15. The recoil value is added to the travel of the die in order to calculate the compression factor.

The following formula is obtained, for example

| | |
|---|---|
| Roller travel on the circumference | 100 mm |
| Die travel | 100 mm + piston |
| relative to the die | = 50 mm |
| Groove filling depth | = 5 mm |
| Roller nip | = 1 mm |

The formula $$\frac{5}{1} \cdot \frac{100}{100+50}$$

yields a compression factor=3.333

The entering angle can then be read off from a table.

In this case, not all the powder entered the groove 5 and was compressed, but, instead, only the powder which was within the range of a smaller entering angle.

During the measuring operation, the force exerted on the load cell 18 and the applied torque on the drive shaft of the press roller 2 are recorded simultaneously.

The pressed powder strip removed from the die can then be further processed into granulate and be pressed to form one or more tablets or be filled into capsules. Alternatively, the powder strip may be drilled in a separate, standardized tablet drilling appliance at various locations according to a defined method. The values obtained, via a comparative table, give information on the tensile strength of the powder strip, this, in turn, being comparable to a corresponding tablet hardness.

So that the behavior can be tested in the case of a defined press force and the resulting roller nip, the abutment 3 is mounted on a linear guide 18.

The motor-driven drive shaft, which cannot be seen and on which the exchangeable press roller 2 is mounted, is located in the bearing block 1. A hydraulic cylinder 19, capable of being mounted in various positions, is mounted, as a moveable carrier for the abutment 3 and the sliding surface 10, on the bearing block 1. The linear guides 18, likewise capable of being mounted in various positions, stabilize the abutment 3 in relation to the press roller axis. The die 4 is provided with a groove 5 which is wider than the press roller 2. The depth of the groove 5 is greater than a 20 degree angle tangent to the press roller, as measured from the horizontal center axis. A transverse slide 6 running tangentially to the roller surface seals off the die 4 and prevents the powder from flowing out undesirably prior to measurement. The groove 5 is covered with a longitudinal slide 7. A stop 8 is set in its vertical position on the clamping piece 9. A piston 11 seals off the groove 5 upward. A guide part 12 prevents the piston 11 from tilting in the groove 5. The guide part 12 and the piston 11 are mounted on the guide rod 13. A tared weight 14 having a permanently installed pointer 15 is mounted at the upper end of the guide rod 13. A holder 16 stabilizes the guide rod 13 in its vertical position. A scale 17 makes it possible to read off the respective position of the piston before and after the process and to evaluate this position for the calculation. Travel measurement may also be carried out electronically or optically. The hydraulic cylinder 19 is subjected to a defined pressure, and the applied force acting on the abutment is calculated from the sum, pressure x area of the hydraulic cylinder. So that the powder can be compacted, the force applied by the hydraulic cylinder must be overcome during entry and the abutment 3 must be displaced in the linear guides. The value by which the abutment 3 is displaced is transmitted to the scale 21 via the rule 20 and is read off as the thickness of the pressed powder.

2 methods are customary for the measurement.

Measuring Method 1:

Either loosely dumped powder, that is to say the basis is the dumping volume of a powder or of a powder mixture, may be tested for the compacting behavior or, according to measuring method 2, the die together with the loosely dumped powder or powder mixture may be precompressed on a calibrated tamping volumenometer at 1250 strokes according to an acknowledged method for determining the tamping volume.

For filling, the die 4 is laid horizontally onto a clean suitable base. The groove 5 opened upward is filled with powder. After the powder has been introduced into the groove 5 of the die 4, the transverse slide 6 and the longitudinal slide 7 are pushed into their guides and the piston 11 is introduced. As a result of the introduction of the transverse slide 6, of the longitudinal slide 7 and of the piston 11, the powder space is closed. The die 4 is raised and pushed toward the press roller 2 until the transverse slide 6 touches the roller surface and the die 4 comes to bear on its rear closed side against the abutment 3. The transverse slide 6 is then removed and the die 4 is pushed downward toward the press roller 2 until the powder comes to bear against the roller surface. The stop 8 of the longitudinal slide 7 will simultaneously rest on the support 9. At this moment, the position of the pointer 15 against the scale 17 is tared and the zero point is thus set. The hydraulic cylinder is pressurized with a defined pressure via a pump which is not shown.

The indication on the rule 21 is set at 0 against the pointer 20 and is tared. Travel measurement may also be carried out electronically or optically.

According to FIG. 2, the travel covered on the circumference of the forward-rotating press roller 2 is equal to the travel of the moving die 4 and the piston 11. This means that the entire powder quantity introduced has been compressed.

Groove filling depth=5 mm

Indication of roller nip on the rule (21) 1 mm

| Groove filling depth | = 5 mm |
|---|---|
| Indication of roller nip on the rule (21) | 1 mm |

$$\frac{5}{1} \cdot \frac{100}{100+0}$$

yields a compression factor=5

The entering angle can then be read off from a table.

The applied press force KN/cm lin. was predefined as a fixed quantity and can be transmitted directly to production machines.

A differential value between the travel of the piston 11 and that on the circumference of the press roller 2, which is equal to the travel of the die 4, is obtained when the powder, because of its changed entering behavior, allows a lower entering angle and therefore causes a recoil value on the piston 11. This recoil value is indicated and read off on the rule 17 via the piston 11, the guide rod 13 and the pointer 15. The recoil value is added to the travel of the die in order to calculate the compression factor.

The following formula is obtained, for example

| Roller travel on the circumference | 100 mm |
|---|---|
| Die travel | 100 mm + piston |
| relative top the die | = 50 mm |
| Groove filling depth | = 5 mm |
| Roller nip | = 1 mm |

The formula $$\frac{5}{1} \cdot \frac{100}{100+50}$$

yields a compression factor=3.333

In this case, not all the powder entered the groove (5) and was; compressed, but, instead, only the powder which was located within the range of a smaller entering angle. The applied press force KN/cm lin. was predetermined as a fixed quantity, and the travel covered by the abutment 3 can be read off on the rule 21 as a resulting nip width.

The applied torque yields a value which can be transmitted directly to production machines when the effective width of the press rollers in cm is multiplied by the measured value. It is more expedient, however, for this value, too, to be defined in Nm/cm of roller width.

The pressed powder strip removed from the die can then be further processed into granulate and be pressed to form one or more tablets or be filled into capsules.

What is claimed is:

1. A method of determining a compression factor of powders for processing by roller presses having roller diameters of 100 to 400 mm, comprising the steps of filling a groove of a die with powder; introducing a piston into the groove; pushing the die on a rotating press roller until it touches a roller surface; opening an end of the die located opposite to the press roller and pushing the die downward on the press roller until the powder rests on the roller surface; during a measurement exerting a force on the piston for compressing the powder; and using a position of the piston in relation to the roller for measuring a compression factor.

2. A method as defined in claim 1, and further comprising a step of compressing the powder filled into the groove in a predetermined gap by the rotating press roller.

3. A method as defined in claim 1, and further comprising compressing the powder filled into the groove by the rotating press roller with a predetermined force.

4. A method as defined in claim 1, and further comprising providing the groove in the die which is displaceable.

5. A method as defined in claim 1, and further comprising moving the piston provided in the groove by a guide part and a guide rod, and indicating a traveled distance on a ruler and a pointer.

6. A method as defined in claim 1, and further comprising moving a hydraulic cylinder which is connected with an abutment, over two linear guides, and indicating a traveled distance on a ruler and a pointer.

7. A method as defined in claim 1, and further comprising fixedly presetting a roller gap, and measuring a resulting force.

8. A method as defined in claim 1, and further comprising fixedly presetting a pressure force, and measuring a resulting gap width.

9. A device for determining a compression factor of powders for processing by roller presses having roller diameters of 100 to 400 mm, the device comprising a die with a groove to be filled with powder; a piston introducable into the groove; a rotating press roller onto which the die is pushed until it touches a roller surface, the die having an end located opposite to the press roller and openable, so that the die is pushed downward on the press roller until the powder rests on the roller surface; means which during a measurement exert a force on the piston for compressing the powder; and means using a position of the piston in relation to the roller for measuring a compression factor.

10. A device as defined in claim 9, wherein said die is displacable relative to said rotating press roller; and further comprising a ruler and a pointer; and a guide part and a guide rod connecting said piston with said ruler and said pointer.

11. A device as defined in claim 10, and further comprising an abutment which is fastened on two linear guides and connected with said roller and said pointer.

12. A device as defined in claim 9, wherein said groove has a depth which is greater than a 20 degree angle tangent to said press roller, measured from a horizontal central axis.

* * * * *